United States Patent
Stopek et al.

(10) Patent No.: US 10,722,224 B2
(45) Date of Patent: Jul. 28, 2020

(54) MEDICAL DEVICE FOR WOUND CLOSURE AND METHOD OF USE

(71) Applicant: Covidien LP, Mansfield, MA (US)

(72) Inventors: Joshua Stopek, Minneapolis, MN (US); Steven L. Bennett, Cheshire, CT (US); Timothy Sargeant, Dublin, CA (US)

(73) Assignee: Covidien LP, Mansfield, MA (US)

( * ) Notice: Subject to any disclaimer, the term of this patent is extended or adjusted under 35 U.S.C. 154(b) by 489 days.

(21) Appl. No.: 15/008,591

(22) Filed: Jan. 28, 2016

(65) Prior Publication Data

US 2016/0135797 A1 May 19, 2016

Related U.S. Application Data

(60) Division of application No. 12/581,995, filed on Oct. 20, 2009, now Pat. No. 9,271,706, which is a (Continued)

(51) Int. Cl.
*A61B 17/00* (2006.01)
*A61B 17/04* (2006.01)
*A61B 17/06* (2006.01)

(52) U.S. Cl.
CPC .............. *A61B 17/0057* (2013.01); *A61B 2017/00606* (2013.01); *A61B 2017/00637* (2013.01); (Continued)

(58) Field of Classification Search
CPC ............ A61B 17/0487; A61B 17/0401; A61B 17/0057; A61B 2017/0404; A61B 2017/06176; A61B 2017/0464; A61B 2017/0417; A61B 2017/00659; A61B 2017/00004; A61B 2017/00654; A61B 2017/00637; A61B 2017/0419; A61B 2017/0403; A61B 2017/0406; A61B 2017/0408; A61B 2017/0414; A61B 2017/0446; A61B 2017/0448; (Continued)

(56) References Cited

U.S. PATENT DOCUMENTS 3,364,200 A 1/1968 Ashton et al.
3,666,750 A 5/1972 Briskin et al.
(Continued)

FOREIGN PATENT DOCUMENTS

EP 0513736 A1 11/1992
EP 0627911 A1 12/1994
(Continued)

OTHER PUBLICATIONS

European Search Report for EP 10251821.4-1269 date of completion is Jan. 25, 2011 (3 pages).
(Continued)

*Primary Examiner* — Dianne Dornbusch

(57) ABSTRACT

A wound closure device for repairing perforations and tissue wall defects is disclosed herein. The wound closure device has a barbed elongate body and a plug member. The wound closure device may further include a foam structure. The wound closure device may also include an inner member which may be a tissue scaffold. A method for closing tissue is also disclosed.

13 Claims, 5 Drawing Sheets

Related U.S. Application Data continuation-in-part of application No. 12/511,462, filed on Jul. 29, 2009, now Pat. No. 9,943,302.

(60) Provisional application No. 61/088,145, filed on Aug. 12, 2008.

(52) U.S. Cl.
CPC ............ *A61B 2017/00659* (2013.01); *A61B 2017/0462* (2013.01); *A61B 2017/06176* (2013.01)

(58) Field of Classification Search
CPC ...... A61B 2017/045; A61B 2017/0451; A61B 2017/0454; A61B 2017/0456; A61B 2017/0461; A61B 2017/0462
See application file for complete search history.

(56) References Cited

U.S. PATENT DOCUMENTS

| | | |
|---|---|---|
| 3,937,223 A | 2/1976 | Roth |
| 4,043,245 A * | 8/1977 | Kaplan ............... F16B 13/0808 411/346 |
| 4,235,238 A | 11/1980 | Ogiu et al. |
| 4,286,497 A * | 9/1981 | Shamah ................. F16B 37/04 411/342 |
| 4,511,478 A | 4/1985 | Nowinski et al. |
| 4,626,253 A | 12/1986 | Broadnax, Jr. |
| 4,657,461 A * | 4/1987 | Smith ................ F16B 13/0808 24/453 |
| 4,663,163 A | 5/1987 | Hou et al. |
| 4,705,040 A | 11/1987 | Mueller et al. |
| 4,744,364 A | 5/1988 | Kensey |
| 4,826,945 A | 5/1989 | Cohn et al. |
| 4,938,763 A | 7/1990 | Dunn et al. |
| 5,053,047 A * | 10/1991 | Yoon .................. A61B 17/0469 606/223 |
| 5,100,992 A | 3/1992 | Cohn et al. |
| 5,160,745 A | 11/1992 | DeLuca et al. |
| 5,162,430 A | 11/1992 | Rhee et al. |
| 5,192,301 A * | 3/1993 | Kamiya ............. A61B 17/0057 604/907 |
| 5,222,976 A | 6/1993 | Yoon |
| 5,269,809 A | 12/1993 | Hayhurst et al. |
| 5,324,775 A | 6/1994 | Rhee et al. |
| 5,342,393 A * | 8/1994 | Stack ................ A61B 17/0057 24/453 |
| 5,350,399 A * | 9/1994 | Erlebacher ......... A61B 17/0057 128/899 |
| 5,370,661 A * | 12/1994 | Branch .............. A61B 17/0401 24/16 R |
| 5,410,016 A | 4/1995 | Hubbell et al. |
| 5,484,913 A | 1/1996 | Stilwell et al. |
| 5,500,000 A | 3/1996 | Feagin et al. |
| 5,505,952 A | 4/1996 | Jiang et al. |
| 5,514,379 A | 5/1996 | Weissleder et al. |
| 5,527,864 A | 6/1996 | Suggs et al. |
| 5,531,759 A * | 7/1996 | Kensey .............. A61B 17/0057 604/15 |
| 5,543,441 A | 8/1996 | Rhee et al. |
| 5,545,178 A * | 8/1996 | Kensey .............. A61B 17/0057 604/15 |
| 5,549,633 A | 8/1996 | Evans et al. |
| 5,550,187 A | 8/1996 | Rhee et al. |
| 5,580,923 A | 12/1996 | Yeung et al. |
| 5,593,422 A | 1/1997 | Muijs Van de Moer et al. |
| 5,601,557 A | 2/1997 | Hayhurst |
| 5,620,461 A | 4/1997 | Muijs Van De Moer et al. |
| 5,626,863 A | 5/1997 | Hubbell et al. |
| 5,643,596 A | 7/1997 | Pruss et al. |
| 5,645,849 A | 7/1997 | Pruss et al. |
| 5,669,935 A * | 9/1997 | Rosenman ......... A61B 17/0487 606/151 |
| 5,681,334 A | 10/1997 | Evans et al. |
| 5,700,277 A * | 12/1997 | Nash .................. A61B 17/0057 128/887 |
| 5,752,974 A | 5/1998 | Rhee et al. |
| 5,810,884 A | 9/1998 | Kim |
| 5,874,500 A | 2/1999 | Rhee et al. |
| 5,916,236 A | 6/1999 | Muijs Van de Moer et al. |
| 6,007,563 A | 12/1999 | Nash et al. |
| 6,022,351 A * | 2/2000 | Bremer ................ A61B 17/688 606/324 |
| 6,152,943 A | 11/2000 | Sawhney |
| 6,162,241 A | 12/2000 | Coury et al. |
| 6,165,201 A | 12/2000 | Sawhney et al. |
| 6,179,862 B1 | 1/2001 | Sawhney |
| 6,270,515 B1 | 8/2001 | Linden et al. |
| 6,280,474 B1 | 8/2001 | Cassidy et al. |
| 6,312,446 B1 | 11/2001 | Huebsch et al. |
| 6,322,580 B1 | 11/2001 | Kanner |
| 6,326,025 B1 | 12/2001 | Sigler et al. |
| 6,348,064 B1 | 2/2002 | Kanner |
| 6,391,060 B1 | 5/2002 | Ory et al. |
| 6,408,656 B1 | 6/2002 | Ory et al. |
| 6,443,964 B1 | 9/2002 | Ory et al. |
| 6,451,032 B1 | 9/2002 | Ory et al. |
| 6,462,169 B1 | 10/2002 | Shalaby |
| 6,478,727 B2 | 11/2002 | Scetbon |
| 6,491,714 B1 | 12/2002 | Bennett |
| 6,500,777 B1 | 12/2002 | Wiseman et al. |
| 6,506,190 B1 | 1/2003 | Walshe |
| 6,508,828 B1 | 1/2003 | Akerfeldt et al. |
| 6,514,534 B1 | 2/2003 | Sawhney |
| 6,533,762 B2 | 3/2003 | Kanner et al. |
| 6,547,806 B1 | 4/2003 | Ding |
| 6,566,406 B1 | 5/2003 | Pathak et al. |
| 6,596,002 B2 | 7/2003 | Therin et al. |
| 6,596,013 B2 * | 7/2003 | Yang .................. A61B 17/0057 606/139 |
| 6,605,294 B2 | 8/2003 | Sawhney |
| 6,656,200 B2 | 12/2003 | Li et al. |
| 6,669,707 B1 * | 12/2003 | Swanstrom ........ A61B 17/0643 606/151 |
| 6,673,093 B1 | 1/2004 | Sawhney |
| 6,695,855 B1 | 2/2004 | Gaston |
| 6,703,047 B2 | 3/2004 | Sawhney et al. |
| 6,794,485 B2 | 9/2004 | Shalaby et al. |
| 6,800,753 B2 | 10/2004 | Kumar |
| 6,818,018 B1 | 11/2004 | Sawhney |
| 6,833,408 B2 | 12/2004 | Sehl et al. |
| 6,860,895 B1 * | 3/2005 | Akerfeldt ........... A61B 17/0057 606/139 |
| 6,936,005 B2 | 8/2005 | Poff et al. |
| 6,969,400 B2 | 11/2005 | Rhee et al. |
| 6,971,252 B2 | 12/2005 | Therin et al. |
| 7,001,126 B2 * | 2/2006 | Lesecq ............... F16B 19/1054 411/340 |
| 7,009,034 B2 | 3/2006 | Pathak et al. |
| 7,021,086 B2 | 4/2006 | Ory et al. |
| 7,021,316 B2 | 4/2006 | Leiboff |
| 7,026,437 B2 | 4/2006 | Shalaby et al. |
| 7,048,738 B1 * | 5/2006 | Wellisz ................ A61B 17/688 606/70 |
| 7,052,713 B2 | 5/2006 | Stimmeder |
| 7,056,333 B2 * | 6/2006 | Walshe .............. A61B 17/0401 606/232 |
| 7,070,858 B2 | 7/2006 | Shalaby et al. |
| 7,129,319 B2 | 10/2006 | Shalaby |
| 7,169,168 B2 * | 1/2007 | Muijs Van De Moer ................. A61B 17/0057 606/213 |
| 7,176,256 B2 | 2/2007 | Rhee et al. |
| 7,182,763 B2 | 2/2007 | Nardella |
| 7,250,057 B2 | 7/2007 | Forsberg |
| 7,288,105 B2 | 10/2007 | Oman et al. |
| 7,331,199 B2 | 2/2008 | Ory et al. |
| 7,347,850 B2 | 3/2008 | Sawhney |
| 7,351,249 B2 | 4/2008 | Hnojewyj et al. |
| 7,488,340 B2 | 2/2009 | Kauphusman et al. |
| 7,621,937 B2 | 11/2009 | Pipenhagen et al. |

(56) References Cited

U.S. PATENT DOCUMENTS

| | | | |
|---|---|---|---|
| 7,744,624 B2 | 6/2010 | Bettuchi | |
| 7,862,585 B2* | 1/2011 | Li | A61B 17/0401 606/232 |
| 7,972,357 B2 | 7/2011 | Bettuchi | |
| 8,007,514 B2* | 8/2011 | Forsberg | A61B 17/0057 606/213 |
| 8,029,532 B2 | 10/2011 | Sirota | |
| 8,083,768 B2 | 12/2011 | Ginn et al. | |
| 8,088,095 B2 | 1/2012 | Hissong et al. | |
| 8,097,017 B2 | 1/2012 | Viola | |
| 8,162,974 B2* | 4/2012 | Eskuri | A61B 17/0057 606/213 |
| 8,216,260 B2* | 7/2012 | Lam | A61B 17/00234 606/153 |
| 8,277,481 B2 | 10/2012 | Kawaura et al. | |
| 8,403,929 B2* | 3/2013 | Weisshaupt | A61B 17/683 606/282 |
| 8,535,349 B2 | 9/2013 | Chen et al. | |
| 8,920,463 B2* | 12/2014 | McGuckin, Jr. | A61B 17/0057 606/213 |
| 9,271,706 B2 | 3/2016 | Stopek et al. | |
| 9,332,976 B2* | 5/2016 | Yribarren | A61B 17/0057 |
| 9,433,438 B2* | 9/2016 | Memmolo | A61B 17/688 |
| 2001/0003158 A1 | 6/2001 | Kensey et al. | |
| 2001/0046476 A1 | 11/2001 | Plochocka | |
| 2002/0106409 A1 | 8/2002 | Sawhney et al. | |
| 2002/0188319 A1 | 12/2002 | Morris et al. | |
| 2002/0198562 A1* | 12/2002 | Akerfeldt | A61B 17/0057 606/213 |
| 2003/0012734 A1 | 1/2003 | Pathak et al. | |
| 2003/0035786 A1 | 2/2003 | Hendriks et al. | |
| 2003/0073663 A1 | 4/2003 | Wiseman et al. | |
| 2003/0125766 A1 | 7/2003 | Ding | |
| 2003/0229349 A1* | 12/2003 | Wellisz | A61B 17/688 606/70 |
| 2004/0001879 A1 | 1/2004 | Guo et al. | |
| 2004/0023842 A1 | 2/2004 | Pathak et al. | |
| 2004/0030354 A1 | 2/2004 | Leung et al. | |
| 2004/0101546 A1 | 5/2004 | Gorman et al. | |
| 2004/0111100 A1* | 6/2004 | Benderev | A61B 17/0401 606/151 |
| 2004/0122456 A1* | 6/2004 | Saadat | A61B 17/00234 606/157 |
| 2004/0176800 A1 | 9/2004 | Paraschac et al. | |
| 2004/0185250 A1 | 9/2004 | John | |
| 2004/0191277 A1 | 9/2004 | Sawhney et al. | |
| 2004/0243052 A1 | 12/2004 | Kauphusman et al. | |
| 2004/0265371 A1 | 12/2004 | Looney et al. | |
| 2005/0169974 A1 | 8/2005 | Tenerz et al. | |
| 2005/0182443 A1 | 8/2005 | Jonn et al. | |
| 2005/0234509 A1 | 10/2005 | Widomski et al. | |
| 2005/0267527 A1 | 12/2005 | Sandoval et al. | |
| 2005/0267533 A1* | 12/2005 | Gertner | A61B 17/0401 606/232 |
| 2005/0273135 A1* | 12/2005 | Chanduszko | A61B 17/0057 606/213 |
| 2005/0283187 A1* | 12/2005 | Longson | A61B 17/0057 606/213 |
| 2006/0034930 A1 | 2/2006 | Khosravi et al. | |
| 2006/0106418 A1 | 5/2006 | Seibold et al. | |
| 2006/0122608 A1 | 6/2006 | Fallin et al. | |
| 2006/0135991 A1* | 6/2006 | Kawaura | A61B 17/0057 606/213 |
| 2006/0142797 A1* | 6/2006 | Egnelov | A61B 17/0057 606/213 |
| 2006/0159733 A1 | 7/2006 | Pendharkar et al. | |
| 2006/0173492 A1 | 8/2006 | Akerfeldt et al. | |
| 2006/0206146 A1* | 9/2006 | Tenerz | A61B 17/0057 606/213 |
| 2006/0229670 A1 | 10/2006 | Bates | |
| 2006/0229672 A1 | 10/2006 | Forsberg | |
| 2006/0229673 A1 | 10/2006 | Forsberg | |
| 2006/0229674 A1 | 10/2006 | Forsberg | |
| 2006/0233869 A1 | 10/2006 | Looney et al. | |
| 2006/0265006 A1 | 11/2006 | White et al. | |
| 2006/0265007 A1 | 11/2006 | White et al. | |
| 2007/0014862 A1 | 1/2007 | Pameijer et al. | |
| 2007/0032823 A1 | 2/2007 | Tegg | |
| 2007/0032824 A1 | 2/2007 | Terwey | |
| 2007/0049971 A1* | 3/2007 | Chin | A61B 17/0401 606/232 |
| 2007/0123817 A1 | 5/2007 | Khosravi et al. | |
| 2007/0135842 A1* | 6/2007 | Van de Moer | A61B 17/0057 606/232 |
| 2007/0150002 A1 | 6/2007 | Szabo et al. | |
| 2007/0167982 A1 | 7/2007 | Gertner et al. | |
| 2007/0173888 A1* | 7/2007 | Gertner | A61B 17/0401 606/232 |
| 2007/0185529 A1 | 8/2007 | Coleman et al. | |
| 2007/0190110 A1 | 8/2007 | Pameijer et al. | |
| 2007/0198059 A1 | 8/2007 | Patel et al. | |
| 2007/0255314 A1 | 11/2007 | Forsberg | |
| 2007/0275073 A1 | 11/2007 | Huey et al. | |
| 2007/0276433 A1 | 11/2007 | Huss | |
| 2008/0004657 A1 | 1/2008 | Obermiller et al. | |
| 2008/0027365 A1 | 1/2008 | Huey | |
| 2008/0071310 A1* | 3/2008 | Hoffman | A61B 17/0057 606/215 |
| 2008/0071311 A1 | 3/2008 | White et al. | |
| 2008/0109034 A1 | 5/2008 | Mather et al. | |
| 2008/0110961 A1 | 5/2008 | Voegele et al. | |
| 2008/0114092 A1 | 5/2008 | Sawhney | |
| 2008/0114395 A1 | 5/2008 | Mathisen et al. | |
| 2008/0140192 A1 | 6/2008 | Humayun et al. | |
| 2008/0160051 A1 | 7/2008 | Sirota | |
| 2008/0194805 A1 | 8/2008 | Vignon et al. | |
| 2008/0208265 A1* | 8/2008 | Frazier | A61B 17/0401 606/326 |
| 2008/0243182 A1* | 10/2008 | Bates | A61B 17/0057 606/213 |
| 2008/0253860 A1* | 10/2008 | McDuff | F16B 13/003 411/344 |
| 2008/0281352 A1 | 11/2008 | Ingenito et al. | |
| 2009/0012558 A1 | 1/2009 | Chen et al. | |
| 2009/0024107 A1 | 1/2009 | Wilson et al. | |
| 2009/0054927 A1 | 2/2009 | Agnew | |
| 2009/0069843 A1 | 3/2009 | Agnew | |
| 2009/0076542 A1 | 3/2009 | Jonn et al. | |
| 2009/0093670 A1* | 4/2009 | Annest | A61B 17/00234 600/16 |
| 2009/0143820 A1* | 6/2009 | Li | A61B 17/0401 606/228 |
| 2009/0326577 A1 | 12/2009 | Johnson et al. | |
| 2010/0036395 A1 | 2/2010 | Miller | |
| 2010/0042144 A1* | 2/2010 | Bennett | A61B 17/0401 606/213 |
| 2010/0049246 A1 | 2/2010 | Obermiller et al. | |
| 2010/0217309 A1 | 8/2010 | Hansen et al. | |
| 2010/0241162 A1 | 9/2010 | Obermiller et al. | |
| 2010/0249827 A1* | 9/2010 | Mavani | A61B 17/0057 606/213 |

FOREIGN PATENT DOCUMENTS

| | | |
|---|---|---|
| EP | 1704878 A2 | 9/2006 |
| EP | 2 143 737 A1 | 1/2010 |
| EP | 2 153 779 A2 | 2/2010 |
| EP | 2 196 193 A1 | 6/2010 |
| EP | 2 233 160 A2 | 9/2010 |
| EP | 2 233 161 A2 | 9/2010 |
| FR | 2839451 A1 | 11/2003 |
| WO | 9403155 A1 | 2/1994 |
| WO | 94/28800 A1 | 12/1994 |
| WO | 2005016176 A2 | 2/2005 |

(56) References Cited

FOREIGN PATENT DOCUMENTS

| WO | 2005110280 A2 | 11/2005 |
|----|---------------|---------|
| WO | 2006009925 A2 | 1/2006  |

OTHER PUBLICATIONS

European Search Report for EP 09 25 1981 date of completion is Sep. 21, 2010 (3 pages).
International Search Report from Application No. EP 08 25 0526 dated Jan. 7, 2009.
European Search Report for EP 12169360.0-1269 date of completion is Jun. 8, 2012 (6 pages).
International Search Report issued in Application EP 11250562.3 dated Dec. 8, 2011.
International Search Report issued in Application EP 11250564.9 dated Dec. 8, 2011.
International Search Report issued in Application EP 11250563.1 dated Dec. 27, 2011.
International Search Report issued in Application EP 11250566.4 dated Dec. 22, 2011.
International Search Report issued in Application EP 11250565.6 dated Dec. 23, 2011.
Raul Zurita et al.: "Triclosan Release from Coated Polyglycolide Threads", Macromolecular Bioscience, vol. 6, No. 1, Jan. 5, 2006, pp. 58-69.
European Search Report for EP 07751966 date of completion is Nov. 5, 2012.
European Search Report for EP 14164895.6-1659/2759265 date of completion is Dec. 8, 2014 (12 pages).
Extended European Search Report corresponding to EP 14 16 4895.6, dated Dec. 16, 2014; (12 pp.).

* cited by examiner

MEDICAL DEVICE FOR WOUND CLOSURE AND METHOD OF USE

CROSS-REFERENCE TO RELATED APPLICATIONS

The present application is a Divisional Application, which claims priority to, and the benefit of, U.S. patent application Ser. No. 12/581,995, filed on Oct. 20, 2009, now U.S. Pat. No. 9,271,706, which is a Continuation-in-Part Application, which claims priority to, and the benefit of, U.S. patent application Ser. No. 12/511,462, filed on Jul. 29, 2009, now U.S. Pat. No. 9,943,302, which claims priority to, and the benefit of, U.S. Provisional Patent Application Ser. No. 61/088,145, filed on Aug. 12, 2008, the entire contents of each of which are hereby incorporated by reference.

BACKGROUND

Technical Field

The present disclosure relates to a medical device and more particularly a wound closure device for repairing perforations in tissue and sealing a tissue wall.

Background of Related Art

A variety of surgical procedures, for example, laparoscopic procedures, are performed through an access port, during which the access port punctures the tissue to provide access to the surgical site.

Currently, wound closure devices such as sutures are used to close various layers of tissue post-surgery. Suturing a patient after removal of an access device may be cumbersome, while accumulating additional costs to the patient such as increased time spent in the operating room.

It would be advantageous to provide a device which enables improved, e.g., faster closure of tissue punctures or tissue perforations for certain procedures.

SUMMARY

The present disclosure describes a wound closure device including an elongate body having a distal portion and a proximal portion, and a plurality of barbs extending from a surface thereof and extending at least partially in a distal direction and a plug member having a tissue facing surface coupled to the distal end of the elongate body. The elongate body, the plug member, or both, may include at least one reactive group, such as, isocyanate, N-hydroxy succinimide, cyanoacrylate, aldehyde, genipin, trilysine, tetralysine, polylysine, diimide, diisocyanate, cyanamide, carbodiimide, dimethyl adipimidate, and combinations thereof. The reactive group on elongate body, the plug member, or both, may include a coating on a portion of a surface of the wound closure device. In embodiments, the elongate body is biodegradable. In embodiments, the elongate body further includes a needle attached to at least one end thereof.

The plug member may include a foam, tissue scaffold, mesh, or hydrogel. In embodiments where the plug member is a hydrogel, the hydrogel may swell from about 5% to about 100% of its original volume. In embodiments where the plug member is a mesh, the mesh may be biodegradable and/or non-biodegradable. The mesh may also be positioned adjacent a tissue facing surface.

In embodiments, the plug member may be configured to change dimension from a first, compressed shape for delivery to a second, expanded shape for placement. The plug member may be shaped so as to limit the movement of the foam structure proximally through a tissue wall. The plug member may include an anti-adhesive coating. The plug member include one or more of proteins, polysaccharides, polynucleotides, poly(alphahydroxy esters), poly(hydroxyl alkanoates), poly(ortho esters), polyurethanes, polylactones, poly(amino acids), cellulose, polyacrylates, polyethylene glycols, polyethylene oxides, and combinations thereof.

The wound closure device may also include an inner member moveably positioned on the elongate body. The device may include a polymer selected from the group consisting of nucleophilic polymers, electrophilic polymers and combinations thereof.

The disclosure also describes a method of closing tissue. The method includes steps of providing a wound closure device having an elongate body, the elongate body including a plurality of barbs formed along the surface thereof and a plug member attached to a distal end of the elongate body, the plug member including a flange portion and a core portion and positioning the wound closure device through a tissue wall such that the flange portion is adjacent to an internal wall of the tissue and the core portion extends into the tissue. The method may also include the step of positioning an inner member interior to an external wall of the tissue, wherein the inner member is flush with the external wall.

BRIEF DESCRIPTION OF DRAWINGS

Various preferred embodiments of the wound closure devices are described herein with reference to the drawings, in which.

DETAILED DESCRIPTION OF EMBODIMENTS

The present disclosure is directed to a medical, e.g., wound closure device. The wound closure device includes an elongate body having a plurality of barbs extending from the surface. In some embodiments, the device includes an inner member and an outer member, each moveably positioned on a proximal portion of the elongate body. In certain embodiments, the wound closure device includes a foam structure, hydrogel or tissue scaffold attached to a distal portion of the elongate body.

In the description that follows, the term "proximal" as used herein, means the portion of the device which is nearer to the user, while the term "distal" refers to the portion of the device which is further away from the user. The term "tissue" as defined herein means various skin layers, muscles, tendons, ligaments, nerves, fat, fascia, bone and different organs.

Figure 1:
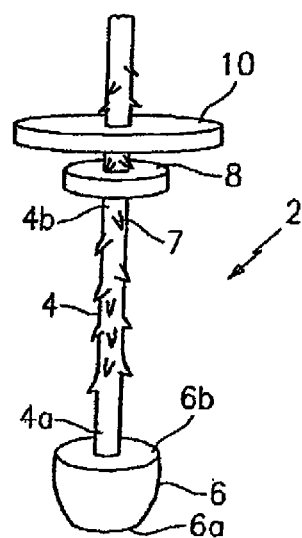
FIG. 1 is a perspective view of one embodiment of a wound closure device in accordance with the present disclosure.

A wound closure device according to one embodiment of the present disclosure is illustrated in FIG. 1. The wound closure device 2 comprises an elongate body 4 which includes a plurality of barbs 7 disposed along a surface of the elongate body 4. The elongate body 4 is generally cylindrical in shape and may have a generally circular cross-sectional area, although other shapes and cross-sectional areas are envisioned. In particular, the elongate body 4 is in the form of a suture and is comprised of a biodegradable polymeric material. A distal portion 4a of the elongate body 4 is connected to a plug member 6. In particular, the elongate body 4 is centrally connected to a relatively flat surface 6b of the plug member 6. Although shown centrally located, the elongate body 4 could also be attached off-center. The elongate body 4 may be connected to the plug member 6 using various methods within the purview of those skilled in the art including, but not limited to, molding, over molding, adhesives and glues (e.g., cyanoacrylates), mechanical connections, male and female locking mechanisms, and the like.

As illustrated in FIG. 1, the plug member 6 is generally conical or hemispherical in shape. A distal portion 6a of the plug member 6 is generally arcuate in shape and once inserted through a tissue wall, the plug member 6 is relatively convex with respect to a tissue wall. A proximal portion 6b of the plug member 6 is generally flat and, in use, is positioned adjacent a tissue wall so as to seal a tissue perforation and prevent fluids from passing through a tissue wall or tissue plane. It should be noted that although the plug member is illustrated as generally conical in shape, this disclosure is not limited to conical-shaped foam structures and other shapes are contemplated. The plug member is large enough, for example, to extend over a tissue perforation created by an access device, for example, an endoluminal device, sealing the tissue wall and limiting fluid passage from a first side of a tissue wall to a second side of a tissue wall. It should also be noted that certain embodiments the plug member may comprise a foam, tissue scaffold or a hydrogel.

Plug members of the present disclosure may be compressible and are capable of undergoing a change in shape. The plug member may be configured to change shape from a first compressed shape when inserted in tissue for delivery to a second, expanded shape for placement. Upon penetration of a tissue wall, the plug member may expand to seal a tissue defect. Plug members of the present disclosure also are shaped so as to limit movement proximally through a tissue wall, once inserted. The plug member may be constructed of a material which expands (swells) from heat or fluid (polymer hydrogels) contact; alternately, the plug member may be mechanically compressed through use of a member such as a sleeve e.g., introducer, wherein upon removal of the sleeve, the plug member expands. Other members including an outer member and an inner member may also be compressible foams which change shape from a first, smaller shape, to a second, larger shape.

Tissue damage or tissue voids may have the potential to form adhesions during certain healing periods. Plug members of the present disclosure may be chemically tailored or coated to have anti-adhesive properties, which may assist in preventing adjacent tissue walls from adhering together, preventing adhesions at a wound site. In various embodiments, the plug structures may be made of anti-adhesive materials. Alternatively, the plug structures may be coated with anti-adhesive materials such as, for example, poly ethylene glycol or hyaluronic acid.

Referring back to FIG. 1, the elongate body 4 has an inner member 8 and, optionally an outer member 10 mounted thereon. The inner member 8 and the outer member 10 are spaced from the distal portion 4a of the elongate body 4. In a preferred embodiment, the inner member 8 and the outer member 10 are located on the proximal portion 4b of the elongate body. Alternately, when the elongate body is longer in length, the inner member and outer member may be moveably mounted on a central portion of the elongate body. Each of the inner member 8 and outer member 10 has an opening extending therethrough and is moveably positioned on the elongate body 4. In situ, the inner member 8 is positioned between a tissue wall (not shown) and the outer member 10. Both the inner member 8 and the outer member 10 are generally shaped like a disc, although other shapes are envisioned. In some embodiments, the inner member 8 may be configured to fill a surface void or tissue defect. The outer member 10 is generally rigid as compared to the inner member 8 so as to affect movement of the inner member 8. In a preferred embodiment, the inner member 8 is comprised of an absorbable polymer such as collagen. The inner member 8 may be in the form of a sheet or a porous material such as foam. The outer member 10 may be of any solid or dense porous material which is rigid, so as to impart movement on the inner member 8 as it is advanced distally along an elongate body 4.

In certain embodiments, at least the inner member 8 may provide a tissue scaffold for cellular infiltration and tissue ingrowth. It is also envisioned that in alternate embodiments, the outer member 10 may provide a scaffold for tissue ingrowth. The tissue scaffold is porous and provides a temporary scaffold/substrate for cell adherence. Tissue scaffolds may be tailored to closely match the mechanical properties of the surrounding tissue intended for regeneration. For example, when the wound closure device is used to close dermal tissue, the scaffold may be mechanically tuned to complement dermal tissue.

In some embodiments, tissue scaffolds, which may comprise either plug members, inner members or both, comprise degradable materials including those listed below, and in certain preferred embodiments the tissue scaffold is collagen. The scaffold degradation profile can be tailored to allow cells to proliferate while the tissue scaffold degrades over time. One skilled in the art can alter the degradation profile of a tissue scaffold by changing various parameters including but not limited to polymer composition and chemistry, density, morphology, molecular weight, size, porosity and pore size, wettability and processing parameters.

As illustrated in FIG. 1, the elongate body 4 further includes a plurality of barbs 7 which may be aligned to enable the wound closure device 2 to move through tissue in one direction while resisting movement through tissue in a generally opposite direction. That is, the barbs 7, extending from the surface of the elongate body 4, permit movement of inner member 8 and outer member 10 in a distal direction while resisting movement of the inner member 8 and outer member 10 in a proximal direction. Additionally, the barbs 7 prevent movement of the plug member 6 towards a proximal portion of the device. Once the plug member 6 of the device 2 is positioned adjacent a tissue wall, the outer member 10 is advanced in a distal direction along the elongate body 4, thereby moving the inner member 8 in a distal direction (with the barbs preventing proximal movement). Once the inner member 8 and outer member 10 are fully distally advanced e.g., contacting a tissue wall, the barbs 7 prevent proximal movement of the inner and outer members (8 and 10), thereby fixating the device 2 against the tissue wall (not shown).

The term "barbs" as used herein encompasses various projections from the surface of an elongate body. Preferably the barbs are formed integrally with the elongate body 4. Barbs extending from the outer surface of the elongate body 4 include but are not limited to projections such as threads, anchors, and teeth. In some embodiments, the barbs are yieldable toward the elongate body 4 of the wound closure device. The barbs can be arranged in any suitable pattern, for example helical, linear, or randomly spaced. The number, configuration, spacing and surface area of the barbs can vary depending upon the tissue type in which the device is used, as well as the composition and geometry of the material utilized to form the device. For example, if the wound closure device is intended to be used in fatty tissue, which is relatively soft, the barbs may be longer and spaced further apart to enable it to grip the soft tissue. The barbs can be arranged in various directions at various angles. In some embodiments, the wound closure device may include a staggered arrangement of large or small barbs.

The shape and/or surface area of the barbs can also vary. For example, fuller-tipped barbs can be made of varying sizes designed for specific surgical applications. In certain applications, such as when closing an access port site and the surgeon is working with fat and relatively soft tissues, larger barbs may be desired, whereas smaller barbs may be more suitable for different procedures with collagen-dense tissues. In some embodiments, a combination of large and small barbs within the same structure may be beneficial, for example when a wound closure device is used in tissue repair with differing layer structures. Use of the combination of large and small barbs on the same device, wherein barb sizes are customized for each tissue layer will ensure maximum holding strength of the device in situ.

Figure 2A:
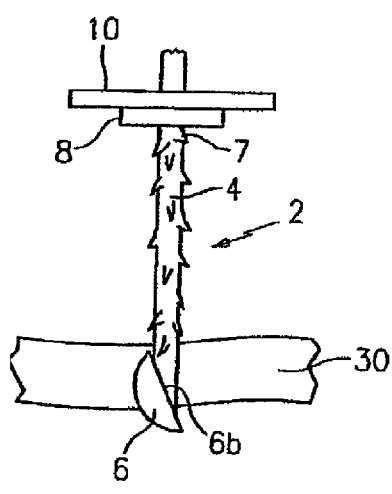
FIGS. 2A-2D are side views of the device of FIG. 1, with portions of tissue removed, showing the steps of placement of the device.
Figure 2B:
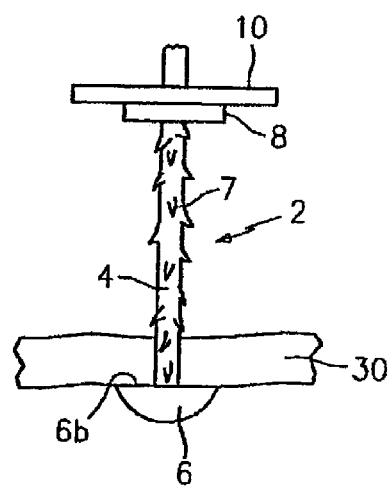

FIGS. 2A and 2B illustrate according to one embodiment, a method by which the wound closure device of FIG. 1 may be positioned in tissue. Note, portions of the tissue are removed for clarity. In FIG. 2A, a device 2 is shown in a first position where a plug member 6 has partially penetrated a tissue wall 30. The device may be inserted into tissue and a distal portion of the device 2 may be inserted through a tissue wall 30 with or without the use of an inserter (not shown). Once the device 2 is completely inserted and the plug member 6 has fully penetrated the tissue wall 30, the proximal portion 6b of the plug member 6 may be rotated (by the user or an insertion device) for positioning against the tissue wall 30 (FIG. 2B). The proximal portion 6b of the plug member 6, which may be generally flat, is positioned adjacent a tissue wall 30 so as to seal a puncture wound and prevent fluids from passing through the tissue wall or tissue plane. It should be noted that the plug member 6 may be inserted in a position so as to minimize tissue contact during delivery. As shown in FIG. 1, the plug member 6 is inserted at an angle and rotated or turned into position against a tissue wall 30; in other embodiments, an inserter may to used which enables the plug member 6 to be inserted in a compressed position so as to minimize tissue contact during delivery.

Figure 2C:
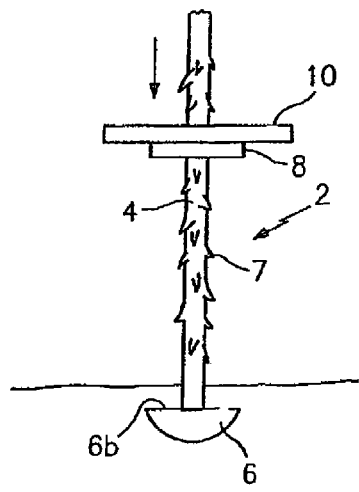
Figure 2D:
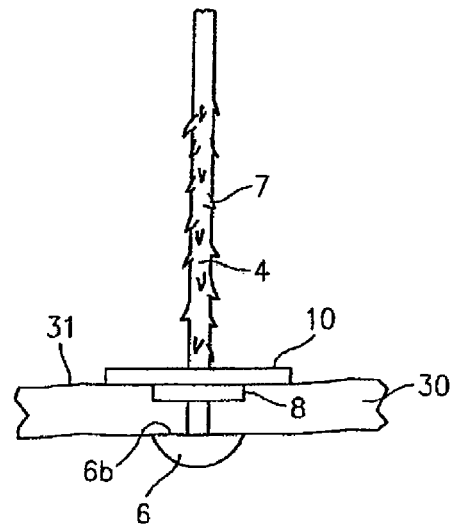

In the next step, an outer member 10 is advanced in a distal direction as indicated by an arrow in FIG. 2C. As previously described, the outer member 10 may be rigid as compared to an inner member 8, and its movement imparts movement of the inner member 8. That is, the outer member 10 is advanced towards the inner member 8 and once in contact, the outer member 10 and the inner member 8 move together over the barbed surface 4 in a distal direction so as to secure the device 2 in tissue (FIG. 2D). In a final position, the inner member 8 is adjacent a tissue surface 31, applying pressure to the tissue surface 31 so as to limit movement of the device 2. As the inner member 8 and the outer member 10 are advanced over the barbed surface 4, the barbs 7 inhibit movement of the inner and outer members (8, 10) in a proximal direction. The barbs 7 may also prevent the foam structure 6 from reversible movement after penetration of the tissue wall 30. It should be noted that although FIGS. 2A-2D illustrate the embodiment described in FIG. 1, other embodiments described herein will be placed in tissue in a similar manner.

Figure 3:
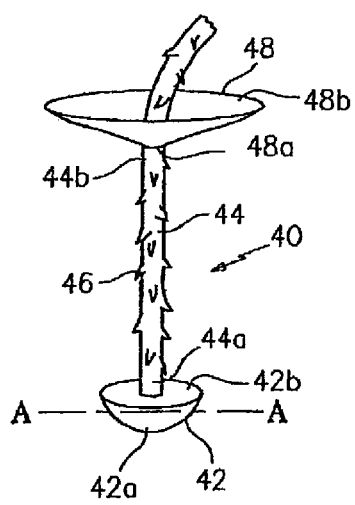
FIG. 3 is an alternate embodiment of a wound closure device in accordance with the present disclosure.
Figure 4:
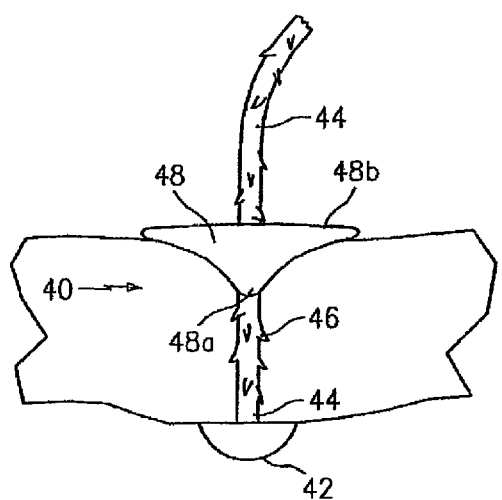
FIG. 4 is a side view of the device of FIG. 3, with portions of tissue removed, showing the device in tissue.

Another embodiment of a wound closure device 40 is shown in FIG. 3. An elongate body 44 is connected at a distal portion 44a to a plug member 42 the elongate body 44 has an outer member 48 mounted thereon, spaced from a distal portion 44a of the elongate body. The plug member 42 may be generally conical or hemispherical in shape, having a generally flat proximal portion 42b and a curved or somewhat pointed distal portion 42a. The plug member 42 is circular in cross-sectional area, taken along line A-A, although other shapes are envisioned. The plug member 42 may be centrally attached to a barbed elongate body 44, or could alternatively be attached off-center. The barbs 46 function in a similar manner as described above and may have various lengths and may be disposed at different angles relative to a surface of the elongate body 44. The outer member 48 has an opening extending therethrough and is rigid enough to move in a distal direction over the barbed elongate body 44. The outer member 48 as shown is funnel-shaped such that a proximal portion 48b has a larger cross-sectional area, which narrows toward a distal portion 48a. In situ, the distal portion 48a may partially penetrate a tissue plane, as illustrated in FIG. 4. The funnel shape of the outer member 48 may assist in further sealing of a tissue defect which may be created by an access device such as an endoscopic device used for Natural Orifice Transluminal Endoscopic Surgery (N.O.T.E.S.). In certain embodiments, the outer member may further include an active agent such as a hemostat.

Figure 6:
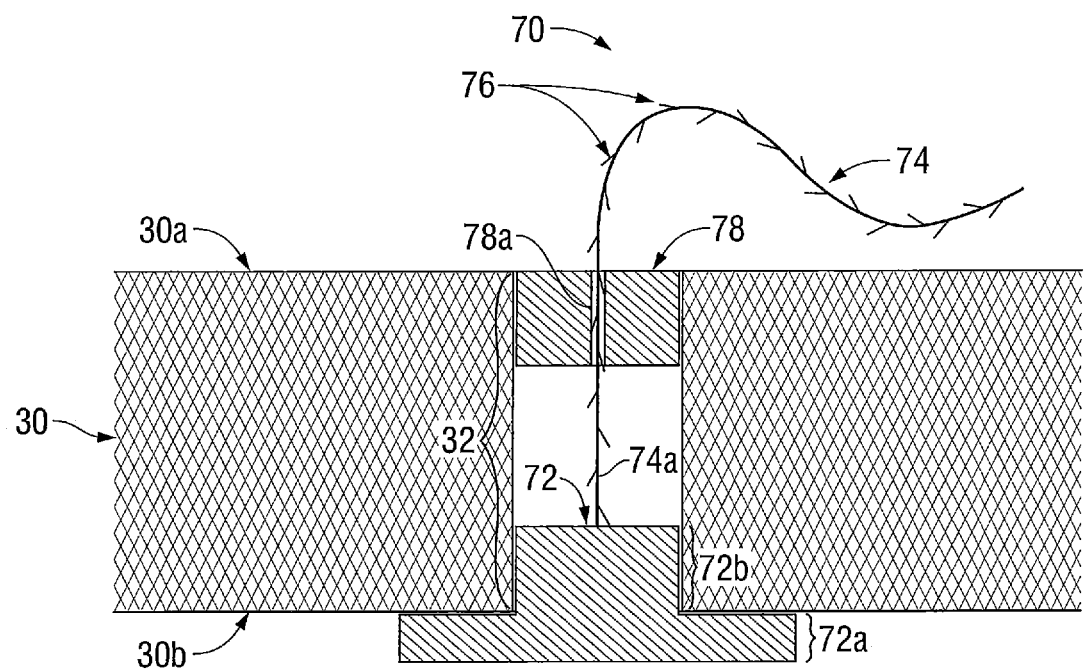
FIG. 6 is a side view of another embodiment of a wound closure device, with portions of tissue removed, in accordance with the present disclosure.

Another embodiment of a wound closure device 70 is shown in FIG. 6. An elongate body 74 is connected at a distal portion 74a thereof to a plug member 72. The elongate body 74 includes barbs 76 extending from a surface thereof. Barbs 76 function in a similar manner to barbs 7 described above and may have various lengths and may be disposed at different angles relative to a surface of the elongate body 74. Elongate body 74 has an inner member 78 slidably mounted thereon, spaced from distal portion 74a of elongate body 74 and from plug member 72. The plug member 72 may be generally shaped like tiered discs, including a flange portion 72a having a first diameter and a core portion 72b having a second, smaller diameter (as compared to the first diameter of flange portion 72a). While substantially cylindrical, monolithically formed portions 72a, 72b of plug member 72 are shown/described, other shapes are envisioned and within the scope of the present application. The plug member 72 may have an opening or passage (not shown) extending therethrough and may be movably positioned on the elongate body 74. In some embodiments, the core portion 72b may be configured to fill a void, defect, or opening 32 in tissue 30. The tissue 30 may include an external wall 30a and an internal wall 30b, which may be separated by opening 32. In situ, the plug member 72 may be positioned such that the flange portion 72a is exterior of opening 32 and generally adjacent to internal wall 30b of tissue 30, while the core portion 72b is disposed within opening 32 formed in tissue 30.

With continued reference to FIG. 6, the inner member 78 has an opening or lumen 78a extending therethrough and is sufficiently rigid to move in a distal direction over the barbed elongate body 74. In situ, the inner member 78 is positioned such that it is at least partially disposed in opening 32 in tissue 30, sealing the tissue opening 32. As shown in FIG. 6, the inner member 78 is disposed within opening 32 in tissue 30 such that inner member 78 is flush with external wall 30a of tissue 30. The inner member 78 may be elliptical in shape and may be configured to fill a void or defect, such as opening 32, in a surface of tissue 30. In some embodiments, the plug member 72 and/or the inner member 78 may further include a hemostatic agent. The plug member 72 and the inner member 78 of the wound closure device 70 may be made of the same materials or different materials.

Figure 7A:
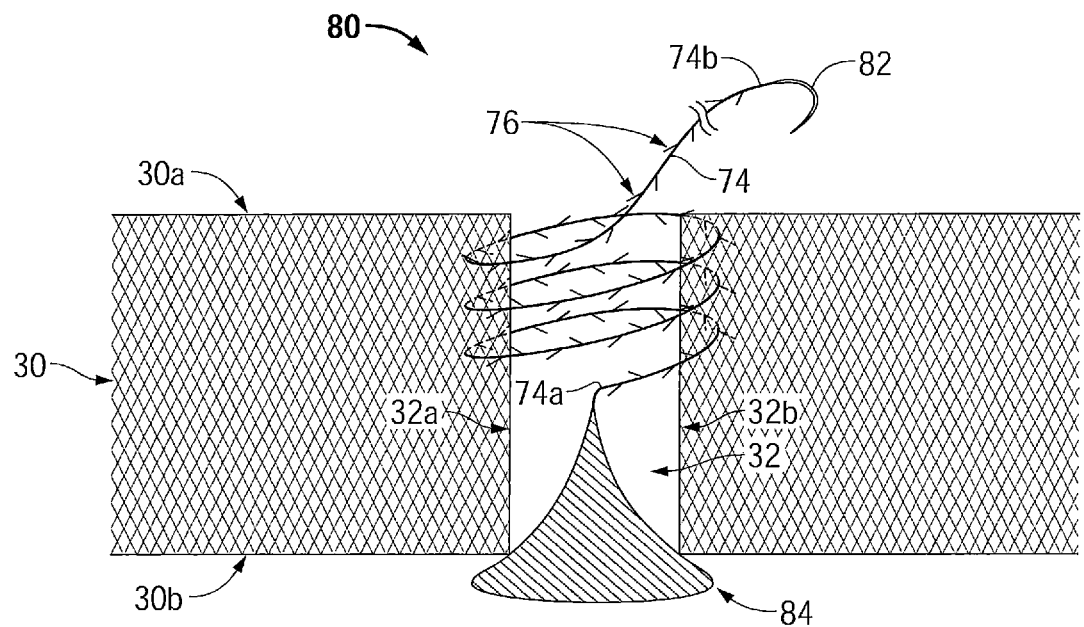
FIGS. 7A-7B are perspective views of another embodiment of the present disclosure, with portions of tissue removed, showing the steps of placement of the device thereof.
Figure 7B:
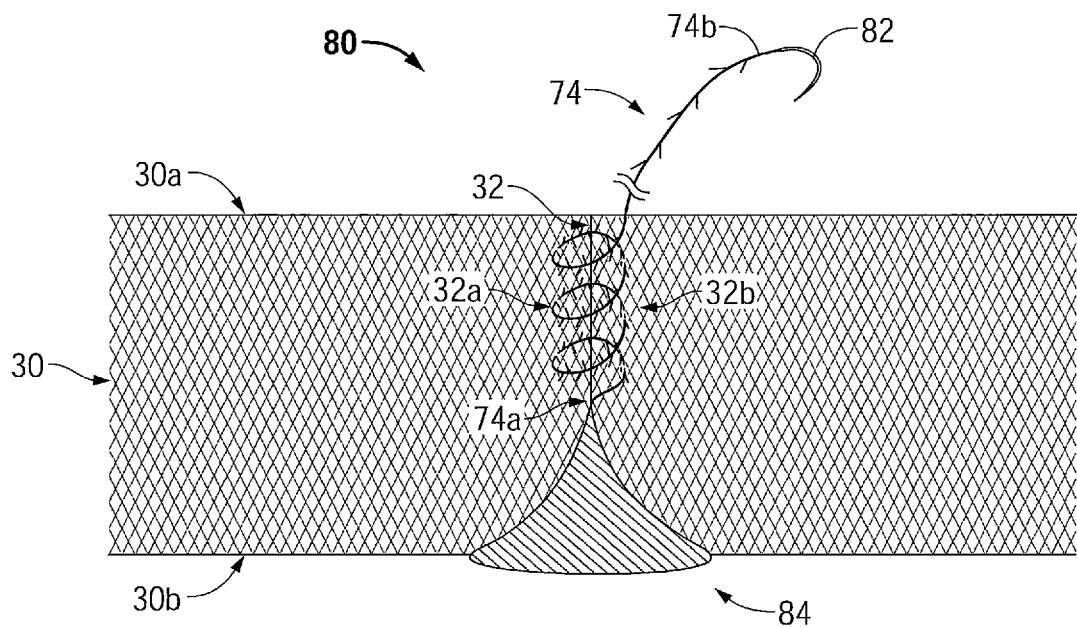

Yet another embodiment of a wound closure device 80 is shown in FIGS. 7A and 7B. Wound closure device 80 includes an elongate body (suture) 74 connected to a plug member 84. The elongate body 74 includes barbs 76 extending from a surface thereof. Barbs 76 function in a similar manner to barbs 7 described above and may have various lengths and may be disposed at different angles relative to a surface of the elongate body 74. More specifically, the elongate body 74 is attached at a distal portion 74a, to the plug member 84, and at a proximal portion 74b to a needle 82. The needle 82 may be any type of surgical needle, for example, such as a straight needle or a curved needle.

In certain embodiments, the plug member 84 may be a hydrogel, tissue scaffold, or foam. The plug member 84 is configured to fill an opening 32 formed in a surface of tissue 30.

The tissue 30 includes an external wall 30a and an internal wall 30b, which may be separated by the opening 32. The opening 32 of tissue 30 includes surfaces 32a and 32b. In situ, the plug member 84 may be inserted into the opening 32 until plug member 84 is at least partially disposed within the opening 32 in tissue 30 such that plug member 84 is flush with internal wall 30b of tissue 30. The needle 82 attached to the proximal end of the elongate body 74 may be used to sew through tissue, securing the surfaces 32a, 32b of tissue together (illustrated in FIG. 7B). Barbs 74 on the elongate body 74 prevent the suture from reversal through tissue 30 and ensure a strong closure.

In one embodiment, the plug member 84 is a hydrogel that swells to fill at least a portion of the opening 32. As shown in a second position (FIG. 7B), the plug member 84 sits substantially flush against surfaces 32a, 32b. The plug member 84 may crosslink to the tissue 30 and/or surfaces 32a, 32b of the opening 32. In other embodiments, the plug member may be a compressible foam or tissue scaffold which may change in shape or swell to uptake fluids while providing a scaffold for tissue integration and wound healing.

Figure 5A:
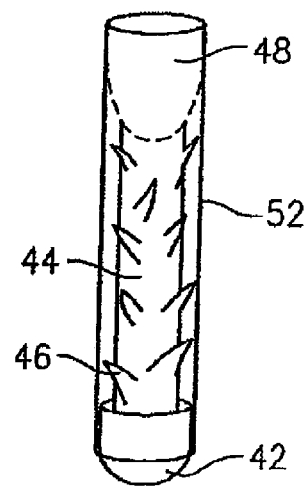
FIG. 5A is a side view of the device of FIG. 3 in a first, compressed shape.
Figure 5B:
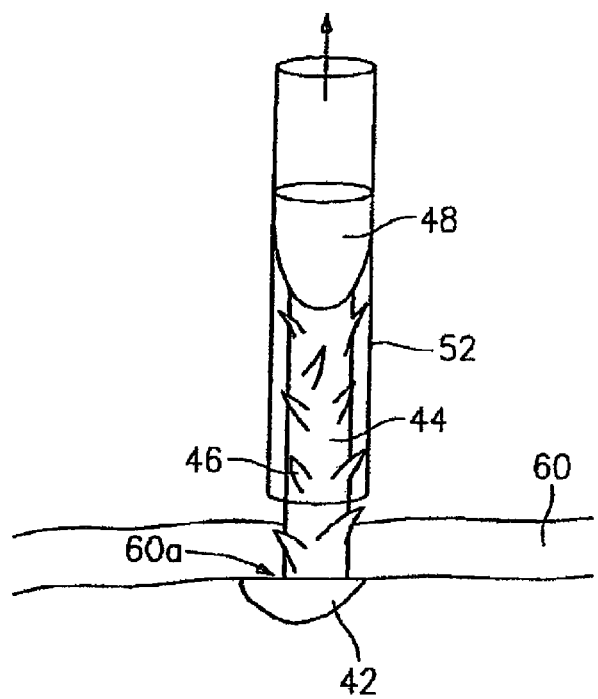
FIG. 5B is a side view of the device of FIG. 3 in tissue, with portions of tissue removed, in a second, expanded shape.

Wound closure devices of the present disclosure may be inserted with the assistance of an introducer (insertion device). By way of example, FIG. 5A illustrates the compression of the wound closure devices of FIGS. 3 and 4, by a sleeve for insertion into tissue. However it is understood that other embodiments of a wound closure device, as described herein, may also be compressed by a sleeve for insertion into tissue. The sleeve 52 of the introducer has a length so as to extend may be employed to retain the plug member 42 in a first, compressed shape for insertion/delivery. The sleeve 52 of the introducer has a length so as to extend over the elongate body 44 and outer member 48. Upon penetrating a tissue wall 60 (FIG. 5B), the sleeve 52 of the introducer may be removed (retracted in the direction of the arrow), allowing the plug member 42 to expand to a second larger shape, extending over a tissue defect 60a, for placement thereof. Once the sleeve 52 of the introducer is removed, the outer member 48 may be advanced in a distal direction, securing the device in place. The sleeve may also keep other members, e.g., inner members and tissue scaffolds, of the device in a compressed position for insertion into a body cavity.

The shape of the device may vary depending upon the condition to be treated. Due to the variability of patient morphology and anatomy, the device may be of any suitable size. In embodiments, the elongate body of the wound closure device may have a length from about 10 mm to about 150 mm and the plug member may have a width from about 5 mm to about 36 mm, in embodiments the elongate body may have a length from about 30 mm to about 80 mm and the plug member may have a width from about 10 mm to about 15 mm, and in other embodiments the elongate body may have a length from at least 10 mm and the plug member may have a width from about at least 5 mm. In one particular embodiment, the elongate body may have a width of about 39 mm and a length of about 50 mm.

Materials used to construct the wound closure devices of the present disclosure may include biodegradable materials, which may be synthetic and/or natural materials. The term "biodegradable" as used herein refers to materials which decompose, or lose structural integrity under body conditions (e.g., enzymatic degradation or hydrolysis). Suitable synthetic biodegradable materials may include, but are not limited to, polymers such as those derived from lactones including lactide, glycolide, caprolactone, and valerolactone; carbonates such as trimethylene carbonate, tetramethylene carbonate, and the like; dioxanones such as 1,4-dioxanone; 1,dioxepanones such as 1,4-dioxepan-2-one and 1,5-dioxepan-2-one; ethylene glycol; ethylene oxide; ester-amides; γ-hydroxyvalerate; β-hydroxypropionate; alpha-hydroxy acid; hydroxybuterates; poly(ortho esters); hydroxy alkanoates; tyrosine carbonates; polyimide carbonates; poly-imino carbonates such as poly(bisphenol A-iminocarbonate) and poly (hydroquinone-iminocarbonate); polyurethanes; polyanhydrides; polymer drugs such as polydiflunisol, polyaspirin, and protein therapeutics; and copolymers and combinations thereof. In one embodiment, the barbed elongate body comprises V-LOC™ wound closure device (Tyco Healthcare Group LP, d/b/a Covidien), a copolymer of about 67% glycolic acid and 33% trimethylene carbonate.

In certain embodiments, wound closure devices according to the present disclosure may be constructed at least in part using shape memory polymers. Suitable polymers used to prepare hard and soft segments of shape memory polymers may include, but are not limited to monomers and polymers such as polycaprolactones; dioxanones; lactides; glycolides; polyacrylates; polyamides; polysiloxanes; polyurethanes; polyether amides; polyurethane/ureas; polyether esters; and urethane/butadiene copolymers; and combinations thereof. For example, the wound plug may comprise shape memory materials which expand the plug upon reaching body temperature, sealing an inner tissue wall.

Suitable natural biodegradable polymers may include, but are not limited to, collagen; poly (amino acids); polysaccharides such as cellulose, dextran, chitin, alginate; glycosaminoglycans; hyaluronic acid; gut; copolymers and combinations thereof. In preferred embodiments, collagen is used to construct the inner member of the medical device.

Collagen as used herein includes natural collagen such as animal derived collagen, or synthetic collagen such as human or bacterial recombinant collagen.

The collagen can be modified by using any method known to those skilled in the art to provide pendant portions of the collagen with moieties which are capable of covalently bonding with the reactive chemical groups of a glycosaminoglycan. Examples of such pendant moieties include aldehydes, sulfones, vinylsulfones, isocyanates, and acid anhydrides. In addition, electrophilic groups such as —CO2N(COCH2)2, —CO2N(COCH2)2, —CO2H, —CHO, —CHOCH2, —N=C=O, —SO2CH CH2, —N(COCH)2, —S—S—(C5H4N) may also be added to pendant chains of the collagen to allow covalent bonding to occur with the glycosaminoglycans.

In some embodiments, the collagen may be modified through the addition of an oxidizing agent. Contacting collagen with an oxidizing agent creates oxidative cleavage along portions of the collagen thereby creating pendant aldehyde groups capable of reacting with the glycosaminoglycans. The oxidizing agent may be, for example, iodine, peroxide, periodic acid, hydrogen peroxide, a periodate, a compound containing periodate, sodium periodate, a diisocyanate compound, a halogen, a compound containing halogen, n-bromosuccinimide, a permanganate, a compound containing permanganate, ozone, a compound containing ozone, chromic acid, sulfuryl chloride, a sulfoxide, a selenoxide, an oxidizing enzyme (oxidase) and combinations thereof. In certain embodiments, the oxidizing agent is periodic acid.

In certain applications it may be preferred to have certain members of the wound closure device comprise non-degradable materials. For example, in embodiments containing mesh, it may be preferred to have the mesh comprise a non-degradable material. In embodiments including an outer member, it may be beneficial for the outer member to be non-degradable. A non-degradable material may be better suited for an external environment, or may provide better resistance against skin flora, compared to certain biodegradable materials. Suitable non-biodegradable materials may be used to construct the wound closure device including, but not limited to, fluorinated polymers (e.g., fluoroethylenes, propylenes, fluoroPEGs), polyolefins such as polyethylene and polypropylene, polyesters such as poly ethylene terephthalate (PET), nylons, polyamides, polyurethanes, silicones, ultra high molecular weight polyethylene (UHMWPE), polybutesters, polyethylene glycol, polyaryletherketone, copolymers and combinations thereof. Additionally, non-biodegradable polymers and monomers may be combined with each other and may also be combined with various biodegradable polymers and monomers to create a composite device.

In some embodiments, the wound closure device may comprise metals (e.g., steel or titanium), metal alloys and the like. In alternate embodiments, the elongate body or outer member may comprise degradable metals such as degradable magnesium.

As previously mentioned, at least a portion of the wound plug may comprise a foam. The foam may have an open cell structure where the pores are connected to each other, forming an interconnected network. Conversely, foams of the present disclosure may be closed cell foams where the pores are not interconnected. Closed cell foams are generally denser. In certain embodiments, the foam structure of the present disclosure is an open cell foam.

In one embodiment, the foam plug includes a material which contains an aliphatic diacid linking two dihydroxy compounds. The dihydroxy compounds which may be utilized include, but are not limited to, polyols including polyalkylene oxides, polyvinyl alcohols, and the like. In some embodiments, the dihydroxy compounds can be a polyalkylene oxide such as polyethylene oxide ("PEO"), polypropylene oxide ("PPO"), block or random copolymers of polyethylene oxide (PEO) and polypropylene oxide (PPO). Suitable aliphatic diacids which may be utilized in forming the foams include, for example, aliphatic diacids having from about 2 to about 8 carbon atoms suitable diacids include, but are not limited to sebacic acid, azelaic acid, suberic acid, pimelic acid, adipic acid, glutaric acid, succinic acid, malonic acid, oxalic acid and combinations thereof.

More specifically, a polyethylene glycol ("PEG") may be utilized as the dihydroxy compound as disclosed in U.S. Patent Application Publication No. 20060253094, the entire disclosure of which is incorporated by reference herein. It may be desirable to utilize a PEG with a molecular weight ranging from about 200 to about 1000, typically from about 400 to about 900. Suitable PEGs are commercially available from a variety of sources under the designations PEG 200, PEG 400, PEG 600 and PEG 900.

The foam member may be formed using any method suitable to forming a foam or sponge including, but not limited to the lyophilization or freeze-drying of a composition. The foam may be cross-linked or non-crosslinked, and may include covalent or ionic bonds. Suitable techniques for making foams are within the purview of those skilled in the art.

In another embodiment, the wound closure device or portions thereof is made from oxidized cellulose. Such materials are known and include oxidized cellulose hemostat materials commercially available under the trade name SURGICEL®. Methods for preparing oxidized cellulose hemostat materials are known in the art and are disclosed, for example in U.S. Pat. Nos. 3,364,200; 4,626,253; 5,484,913; and 6,500,777, the disclosures of which are incorporated herein by this reference in their entirety.

Aside from a foam, the plug member may include a pre-formed hydrogel or mesh. The hydrogel, mesh or foam forming the plug member may adhere or cross-link with any plane of the tissue. The planes of the tissue include, for example, the external wall of the tissue, the internal wall of the tissue, and any portion of tissue exposed by an opening, void, or defect in the tissue walls.

In certain embodiments, the wound plugs may additionally comprise a mesh component. In some embodiments, the mesh may form a portion of the elongate body and/or plug member, for example a layer on a surface thereof. In embodiments, the mesh may include reactive groups as described herein. In embodiments, the plug member may include a non-biodegradable mesh.

The mesh may comprise natural or synthetic, bioabsorbable or non-bioabsorbable materials including those listed below. Suitable meshes include a collagen composite mesh such as Parietex™ (Tyco Healthcare Group LP, dba Covidien) may be used. Parietex™ Composite mesh is a 3-dimensional polyester weave with a resorbable collagen film bonded on one side. In embodiments, the mesh component may comprise a substantially flat sheet. In other embodiments, the mesh component may be cylindrical in shape. Cylindrical mesh components may be formed by rolling a flat sheet of mesh to form a hollow cylinder.

Mesh may comprise filaments such as monofilaments or multi-filaments. Where multi-filament constructs are utilized, they may be plaited, braided, weaved, twisted, and the like, or laid parallel to form a unit for further construction into a fabric, textile, patch, mesh, and the like. The distribution of the filaments or strands may be random or oriented.

Techniques for forming a mesh are within the purview of those skilled in the art and include, for example, casting, molding, needle-punching, hooking, weaving, rolling, pressing, bundling, braiding, spinning, piling, knitting, felting, drawing, splicing, cabling, extruding, and/or combinations thereof.

The mesh thus produced may have a thickness of from about 0.2 mm to about 5 mm, in embodiments from about 1 mm to about 3 mm. The strands may be spaced apart to form pores of from about 100 microns to about 2000 microns in diameter, in embodiments, from about 200 microns to about 1500 microns, in other embodiments from about 750 microns to about 1250 microns in diameter. Examples of various meshes include those disclosed in U.S. Pat. Nos. 6,596,002, 6,408,656, 7,021,086, 6,971,252, 6,695,855, 6,451,032, 6,443,964, 6,478,727, 6,391,060, and U.S. Patent Application Publication No. 2007/0032805, the entire disclosures of each of which are incorporated by reference herein.

The mesh may act as a tissue scaffold, thereby providing a means for tissue integration/ingrowth. Tissue scaffolds also are capable of providing cells with growth and development components. Thus, where the hydrogel of the present disclosure is utilized as a tissue scaffold, it may assist in native tissue regrowth by providing the surrounding tissue with needed nutrients and bioactive agents. In some embodiments, as discussed herein, the hydrogel itself may include a natural component such as collagen, gelatin, hyaluronic acid, combinations thereof, and the like, and thus the natural component may be released or otherwise degrade at the site of implantation as the tissue scaffold degrades.

In embodiments, the elongate body, the plug member, or both, may be formed from a hydrogel (likewise coated with a hydrogel). The hydrogel may be formed of any components within the purview of those skilled in the art. In some embodiments, as discussed further below, the hydrogel may be formed of a natural component such as collagen, gelatin, serum, hyaluronic acid, combinations thereof, and the like. The natural component may degrade or otherwise be released at the site of implantation. The term "natural component" as used herein includes polymers, compositions of matter, materials, combinations thereof, and the like, which can be found in nature or derived from compositions and/or organisms found in nature. Natural components may also include compositions which are found in nature but can be synthesized by man, for example, using methods to create natural/synthetic/biologic recombinant materials, as well as methods capable of producing proteins with the same sequences as those found in nature, and/or methods capable of producing materials with the same structure and components as natural materials, such as synthetic hyaluronic acid, which is commercially available, for example, from Sigma Aldrich.

The hydrogels may be formed from a single precursor or multiple precursors. This may occur prior to implantation or at the time of implantation. In either case, the formation of the hydrogel may be accomplished by having a precursor that can be activated at the time of application to create, in embodiments, a hydrogel. Activation can be through a variety of methods including, but not limited to, environmental changes such as pH, ionicity, pressure, temperature, etc. In other embodiments, the components for forming a hydrogel may be contacted outside the body and then introduced into a patient as an implant such as a pre-formed wound closure device or component thereof.

Where the hydrogel is formed from multiple precursors, for example two precursors, the precursors may be referred to as a first and second hydrogel precursor. The terms "first hydrogel precursor" and "second hydrogel precursor" each mean a polymer, functional polymer, macromolecule, small molecule, or crosslinker that can take part in a reaction to form a network of crosslinked molecules, e.g., a hydrogel.

In embodiments, the precursor utilized to form the hydrogel may be, e.g., a monomer or a macromer. One type of precursor may have a functional group that is an electrophile or nucleophile. Electrophiles react with nucleophiles to form covalent bonds. Covalent crosslinks or bonds refer to chemical groups formed by reaction of functional groups on different polymers that serve to covalently bind the different polymers to each other. In certain embodiments, a first set of electrophilic functional groups on a first precursor may react with a second set of nucleophilic functional groups on a second precursor. When the precursors are mixed in an environment that permits a reaction (e.g., as relating to pH, temperature, ionicity, and/or solvent), the functional groups react with each other to form covalent bonds. The precursors become crosslinked when at least some of the precursors can react with more than one other precursor. For instance, a precursor with two functional groups of a first type may be reacted with a crosslinking precursor that has at least three functional groups of a second type capable of reacting with the first type of functional groups.

The term "functional group" as used herein refers to groups capable of reacting with each other to form a bond. In embodiments, such groups may be electrophilic or nucleophilic. Electrophilic functional groups include, for example, N-hydroxysuccinimides, sulfosuccinimides, carbonyldiimidazole, sulfonyl chloride, aryl halides, sulfosuccinimidyl esters, N-hydroxysuccinimidyl esters, succinimidyl esters, epoxides, aldehydes, maleimides, imidoesters and the like. In embodiments, the electrophilic functional group is a succinimidyl ester.

The first and second hydrogel precursors may have biologically inert and water soluble cores. More specifically, the electrophilic hydrogel precursors may have biologically inert and water soluble cores, as well as non-water soluble cores. When the core is a polymeric region that is water soluble, suitable polymers that may be used include: polyethers, for example, polyalkylene oxides such as polyethylene glycol ("PEG"), polyethylene oxide ("PEO"), polyethylene oxide-co-polypropylene oxide ("PPO"), co-polyethylene oxide block or random copolymers, and polyvinyl alcohol ("PVA"); poly(vinyl pyrrolidinone) ("PVP"); poly (amino acids); poly(saccharides), such as dextran, chitosan, alginates, carboxymethylcellulose, oxidized cellulose, hydroxyethylcellulose, hydroxymethylcellulose; hyaluronic acid; and proteins such as albumin, collagen, casein, and gelatin. Other suitable hydrogels may include components such as methacrylic acid, acrylamides, methyl methacrylate, hydroxyethyl methacrylate, combinations thereof, and the like. In embodiments, combinations of the foregoing polymers and components may be utilized.

The polyethers, and more particularly poly (oxyalkylenes) or polyethylene glycol, may be utilized in some embodiments. When the core is small in molecular nature, any of a variety of hydrophilic functionalities can be used to make the first and second hydrogel precursors water soluble. For example, functional groups like hydroxyl, amine, sulfonate and carboxylate, which are water soluble, may be used to make the precursor water soluble. For example, the n-hydroxysuccinimide ("NHS") ester of subaric acid is insoluble in water, but by adding a sulfonate group to the succinimide ring, the NHS ester of subaric acid may be made water soluble, without affecting its reactivity towards amine groups. In embodiments, the precursor having electrophilic functional groups may be a PEG ester.

As noted above, each of the first and second hydrogel precursors may be multifunctional, meaning that they may include two or more electrophilic or nucleophilic functional groups, such that, for example, a nucleophilic functional group on the first hydrogel precursor may react with an electrophilic functional group on the second hydrogel precursor to form a covalent bond. At least one of the first or second hydrogel precursors includes more than two functional groups, so that, as a result of electrophilic-nucleophilic reactions, the precursors combine to form cross-linked polymeric products, in embodiments, hydrogels.

A macromolecule having the electrophilic functional group may be multi-armed. For example, the macromolecule may be a multi-armed PEG having four, six, eight, or more arms extending from a core. The core may be the same or different from the macromolecule forming the arms. For example, the core may be PEG and the multiple arms may also be PEG. In embodiments, the core may be a natural polymer.

The molecular weight (MW) of the electrophilic crosslinker may be from about 2,000 to about 100,000; in embodiments from about 10,000 to about 40,000. Multi-arm precursors may have a molecular weight that varies depending on the number of arms. For example, an arm having a 1000 MW of PEG has enough CH2CH2O groups to total at least 1000 MW. The combined molecular weight of an individual arm may be from about 250 to about 5,000; in embodiments from about 1,000 to about 3,000; in embodiments from about 1,250 to about 2,500. In embodiments, the electrophilic crosslinker may be a multi-arm PEG functionalized with multiple NHS groups having, for example, four, six or eight arms and a molecular weight from about 5,000 to about 25,000. Other examples of suitable precursors are described in U.S. Pat. Nos. 6,152,943; 6,165,201; 6,179,862; 6,514,534; 6,566,406; 6,605,294; 6,673,093; 6,703,047; 6,818,018; 7,009,034; and 7,347,850, the entire disclosures of each of which are incorporated herein by reference.

The electrophilic precursor may be a cross-linker that provides an electrophilic functional group capable of bonding with nucleophiles on another component, such as, in certain embodiments, a natural component containing primary amines. The natural component may be endogenous (to the patient, for example collagen) to which the electrophilic crosslinker is applied.

In embodiments, one of the precursors may be a nucleophilic precursor possessing nucleophilic groups. Nucleophilic groups which may be present include, for example, —NH2, —SH, —OH, —PH2, and —CO—NH—NH2. Any monomer, macromer, polymer, or core described above as suitable for use in forming the electrophilic precursor may be functionalized with nucelophilic groups to form a nucleophilic precursor. In other embodiments, a natural component possessing nucleophilic groups such as those listed above may be utilized as the nucleophilic precursor.

The natural component may be, for example, collagen, gelatin, blood (including serum, which may be whole serum or extracts therefrom), hyaluronic acid, proteins, albumin, other serum proteins, serum concentrates, platelet rich plasma (prp), combinations thereof, and the like. Additional suitable natural components which may be utilized or added to another natural component include, for example, stem cells, DNA, RNA, enzymes, growth factors, peptides, polypeptides, antibodies, other nitrogenous natural molecules, combinations thereof, and the like. Other natural components may include derivatives of the foregoing, for example modified polysaccharides such as hyaluronic acid or dextran, which may be naturally derived, synthetic, or biologically derived. For example, in some embodiments, the natural component may be aminated hyaluronic acid.

In embodiments, any of the above natural components may be synthetically prepared, e.g., synthetic hyaluronic acid, which may be purchased from Sigma Aldrich, for example. Similarly, in embodiments the natural component could be a natural or synthetic long chain aminated polymer.

The natural component may provide cellular building blocks or cellular nutrients to the tissue that it contacts in situ. For example, serum contains proteins, glucose, clotting factors, mineral ions, and hormones which may be useful in the formation or regeneration of tissue.

In embodiments, the natural component includes whole serum. In some embodiments, the natural component is autologous, e.g., collagen, serum, blood, and the like.

In embodiments, a multifunctional nucleophilic polymer, such as a natural component having multiple amine groups, may be used as a first hydrogel precursor and a multifunctional electrophilic polymer, such as a multi-arm PEG functionalized with multiple NHS groups, e.g., a PEG ester, may be used as a second hydrogel precursor. In embodiments, the precursors may be in solution(s), which may be combined to permit formation of the hydrogel. Any solutions utilized as part of the in situ forming material system should not contain harmful or toxic solvents. In embodiments, the precursor(s) may be substantially soluble in a solvent such as water to allow application in a physiologically-compatible solution, such as buffered isotonic saline.

In some embodiments, a pre-formed hydrogel may be formed from a combination of collagen and gelatin as the natural component, with a multi-functional PEG utilized as a crosslinker. In embodiments, the collagen and gelatin may be placed in solution, utilizing a suitable solvent. To this solution, hyaluronic acid may be added along with a high pH buffer. Such a buffer may have a pH from about 8 to about 12, in embodiments from about 8.2 to about 9. Examples of such buffers include, but are not limited to, borate buffers, and the like.

In a second solution, an electrophilic crosslinker, in embodiments a multi-arm PEG functionalized with electrophilic groups such as n-hydroxysuccinimide, may be prepared in a buffer such as Hanks Balanced Salt Solution, Dulbecco's Modified Eagle's Medium, Phosphate Buffered Saline, water, phosphate buffer, combinations thereof, and the like. The electrophilic crosslinker, in embodiments a multi-arm PEG functionalized with n-hydroxysuccinimide groups, may be present in a solution including the above buffer at a concentration from about 0.02 grams/ml to about 0.5 grams/ml, in embodiments from about 0.05 grams/ml to about 0.3 grams/ml.

The two components may be combined, wherein the electrophilic groups on the multi-arm PEG crosslink the amine nucleophilic components of the collagen and/or gelatin. The ratio of natural component to electrophilic component may be from about 0.01:1 to about 100:1, in embodiments from about 1:1 to about 10:1.

The nucleophilic component, in certain embodiments, the natural components, e.g., collagen, gelatin, and/or hyaluronic acid, may together be present at a concentration of at least about 1.5 percent by weight of the hydrogel, in embodiments from about 1.5 percent by weight to about 20 percent by weight of the hydrogel, in other embodiments from about 2 percent by weight to about 10 percent by weight of the hydrogel. In certain embodiments, collagen may be present from about 0.5 percent to about 7 percent by weight of the hydrogel, in further embodiments, from about 1 percent to about 4 percent by weight of the hydrogel. In another embodiment, gelatin may be present from about 1 percent to about 20 percent by weight of the hydrogel, in further embodiments, from about 2 percent to about 10 percent by weight of the hydrogel. In yet another embodiment, hyaluronic acid and collagen combined as the natural component(s) may be present from about 0.5 percent to about 8 percent by weight of the hydrogel, in further embodiments, from about 1 percent to about 5 percent by weight of the hydrogel. It is also envisioned that the hyaluronic acid may not be present as a "structural" component, but as more of a bioactive agent. For example, hyaluronic acid may be present in solution/gel in concentrations as low as 0.001 percent by weight of the solution/gel and have biologic activity.

The electrophilic crosslinker may be present in amounts of from about 0.5 percent by weight to about 20 percent by weight of the hydrogel, in embodiments from about 1.5 percent by weight to about 15 percent by weight of the hydrogel.

The hydrogels may be formed either through covalent, ionic or hydrophobic bonds. Physical (non-covalent) crosslinks may result from complexation, hydrogen bonding, desolvation, Van der Waals interactions, ionic bonding, combinations thereof, and the like, and may be initiated by mixing two precursors that are physically separated until combined in situ, or as a consequence of a prevalent condition or change in the physiological environment, including temperature, pressure, pH, ionic strength, combinations thereof, and the like. Thus, the hydrogel may be sensitive to these environmental conditions/changes. Chemical (covalent) crosslinking may be accomplished by any of a number of mechanisms, including: free radical polymerization, condensation polymerization, anionic or cationic polymerization, step growth polymerization, electrophile-nucleophile reactions, combinations thereof, and the like.

In some embodiments, hydrogel systems may include biocompatible multi-precursor systems that spontaneously crosslink when the precursors are mixed, but wherein the two or more precursors are individually stable for the duration of the deposition process. In other embodiments, hydrogels may be formed from a single precursor that crosslinks with endogenous materials and/or tissues.

The crosslinking density of the resulting hydrogel may be controlled by the overall molecular weight of the crosslinker and natural component and the number of functional groups available per molecule. A lower molecular weight between crosslinks, such as 600 daltons (Da), will give much higher crosslinking density as compared to a higher molecular weight, such as 10,000 Da. Elastic gels may be obtained with higher molecular weight natural components with molecular weights of more than 3000 Da.

The crosslinking density may also be controlled by the overall percent solids of the crosslinker and natural component solutions. Increasing the percent solids increases the probability that an electrophilic group will combine with a nucleophilic group prior to inactivation by hydrolysis. Yet another method to control crosslink density is by adjusting the stoichiometry of nucleophilic groups to electrophilic groups. A one to one ratio may lead to the highest crosslink density, however, other ratios of reactive functional groups (e.g., electrophile:nucleophile) are envisioned to suit a desired formulation.

The hydrogel thus produced may be bioabsorbable. For example, hydrogels of the present disclosure may be absorbed from about one day to about 18 months or longer. Absorbable polymers materials include both natural and synthetic polymers, as well as combinations thereof.

In embodiments, one or more precursors having biodegradable linkages present in between functional groups may be included to make the hydrogel biodegradable or absorbable. In some embodiments, these linkages may be, for example, esters, which may be hydrolytically degraded. The use of such linkages is in contrast to protein linkages that may be degraded by proteolytic action. A biodegradable linkage optionally also may form part of a water soluble core of one or more of the precursors. Alternatively, or in addition, functional groups of precursors may be chosen such that the product of the reaction between them results in a biodegradable linkage. For each approach, biodegradable linkages may be chosen such that the resulting biodegradable biocompatible crosslinked polymer degrades or is absorbed in a desired period of time. Generally, biodegradable linkages may be selected that degrade the hydrogel under physiological conditions into non-toxic or low toxicity products.

Biodegradable gels utilized in the present disclosure may degrade due to hydrolysis or enzymatic degradation of the biodegradable region, whether part of the natural component or introduced into a synthetic electrophilic crosslinker. The degradation of gels containing synthetic peptide sequences will depend on the specific enzyme and its concentration. In some cases, a specific enzyme may be added during the crosslinking reaction to accelerate the degradation process. In the absence of any degradable enzymes, the crosslinked polymer may degrade solely by hydrolysis of the biodegradable segment. In embodiments in which polyglycolate is used as the biodegradable segment, the crosslinked polymer may degrade in from about 1 day to about 30 days depending on the crosslinking density of the network. Similarly, in embodiments in which a polycaprolactone-based crosslinked network is used, degradation may occur over a period of time from about 1 month to about 8 months. The degradation time generally varies according to the type of degradable segment used, in the following order: polyglycolate<polylactate<polytrimethylene carbonate<polycaprolactone. Thus, it is possible to construct a hydrogel with a desired degradation profile, from a few days to months, using different degradable segments.

Where utilized, the hydrophobicity generated by biodegradable blocks such as oligohydroxy acid blocks or the hydrophobicity of PPO blocks in PLURONIC™ or TETRONIC™ polymers utilized to form the electrophilic precursor may be helpful in dissolving small organic drug molecules. Other properties which will be affected by incorporation of biodegradable or hydrophobic blocks include: water absorption, mechanical properties and thermosensitivity.

In other embodiments, the precursors utilized to form the hydrogel may be non-degradable, e.g., they may include any of the macromers, polymers or cores described above as suitable for use in forming the electrophilic precursor, but possess no ester or other similar degradable linkage. The non-biodegradable linkages may be created through the reaction of an N-hydroxysuccinimidyl carbonate. In one embodiment, the reaction of a multi-arm polyol with a N, N'-dihydroxysuccinimidyl carbonate creates an N-hydroxysuccinimidyl carbonate. The N-hydroxysuccinimidyl carbonate can then be further reacted with a high molecular weight polyamine such as collagen, aminated hyaluronic acid, gelatin, dextran and to create the pre-formed hydrogel. High molecular weight polyamines may provide longer implant stability as compared to lower molecular weight polyamines. High molecular weight polyamines may comprise molecular weights from about 15,000 g/mol to about 250,000 g/mol, in certain embodiments, from about 75,000 g/mol to about 150,000 g/mol. It should be understood that when a non-biodegradable linkage is used, the implant is still biodegradable through use of a biodegradable first hydrogel precursor such as collagen. For example, the collagen may be enzymatically degraded, breaking down the hydrogel, which is then subsequentlly eroded.

Synthetic materials that are readily sterilized and avoid the dangers of disease transmission involved in the use of natural materials may also be used. Indeed, certain polymerizable hydrogels made using synthetic precursors are within the purview of those skilled in the art, e.g., as used in commercially available products such as FOCALSEAL® (Genzyme, Inc.), COSEAL® (Angiotech Pharmaceuticals), and DURASEAL® (Confluent Surgical, Inc). Other known hydrogels include, for example, those disclosed in U.S. Pat. Nos. 6,656,200; 5,874,500; 5,543,441; 5,514,379; 5,410,016; 5,162,430; 5,324,775; 5,752,974; and 5,550,187.

As noted above, in embodiments a multi-arm PEG, sometimes referred to herein as a PEG star, may be included to form a hydrogel utilized in forming at least a portion of a wound closure device of the present disclosure. A PEG star may be functionalized so that its arms include biofunctional groups such as amino acids, peptides, antibodies, enzymes, drugs, or other moieties in its cores, its arms, or at the ends of its arms. The biofunctional groups may also be incorporated into the backbone of the PEG, or attached to a reactive group contained within the PEG backbone. The binding can be covalent or non-covalent, including electrostatic, thiol mediated, peptide mediated, or using known reactive chemistries, for example, biotin with avidin.

Amino acids incorporated into a PEG star may be natural or synthetic, and can be used singly or as part of a peptide. Sequences may be utilized for cellular adhesion, cell differentiation, combinations thereof, and the like, and may be useful for binding other biological molecules such as growth factors, drugs, cytokines, DNA, antibodies, enzymes, combinations thereof, and the like. Such amino acids may be released upon enzymatic degradation of the PEG star.

These PEG stars may also include functional groups as described above to permit their incorporation into a hydrogel. The PEG star may be utilized as the electrophilic crosslinker or, in embodiments, be utilized as a separate component in addition to the electrophilic crosslinker described above. In embodiments, the PEG stars may include electrophilic groups that bind to nucleophilic groups. As noted above, the nucleophilic groups may be part of a natural component utilized to form a hydrogel of the present disclosure.

The wound closure device in accordance with the present disclosure may also be prepared from a polymer having at least one functional group known to have click reactivity, capable of reacting via click chemistry. Click chemistry refers to a collection of reactive groups having a high chemical potential energy capable of producing highly selective, high yield reactions. Examples of click chemistry which may be utilized with a device of the present disclosure include those disclosed in U.S. patent application Ser. No. 12/368,415, the entire disclosure of which is hereby incorporated by reference herein.

The elongate body and/or plug member, and/or a coating on a portion thereof, may thus be formed from one precursor (as by free radical polymerization), two precursors, or made with three or more precursors, with one or more of the precursors participating in crosslinking to form the elongate body and/or plug member, or participating to form a coating or layer over the elongate body and/or plug member. The reactive groups may be applied to the wound closure device utilizing a variety of means including but not limited to spray coating, dip coating, melt pressing, extrusion or co-extrusion, etc. The reactive groups may be in the form of solids, liquids, powders or particulates.

The elongate body and plug member of the wound closure device may provide wound closure by any of a variety of chemical and/or physical means. The elongate body and/or plug member may include reactive groups on its surface to bind to tissue, or a pre-treated moiety may be applied to the tissue surface that will bond with the device upon implantation.

In embodiments, the elongate body and/or plug member may include dried components, precursors and/or reactive components as described herein, optionally in particle form. These dry materials may be activated by the presence of aqueous physiological fluids. For example, the precursors and/or reactive components may be applied in a dry form, such as particulate matter or in a solid or semi-solid state such as a film or foam. In embodiments, at least one of the first or second hydrogel precursors may be provided as a film on a wound closure device of the present disclosure. These dried precursors may be applied to, or embedded within, for example, a mesh utilized as a component or a portion of a component of a wound closure device of the present disclosure. Upon introduction into a wound, body fluids may provide the necessary moisture to initiate reaction of the precursors and/or reactive components with each other and/or tissue. In embodiments, this reaction may also result in an expansion of the volume of the elongate body, the plug member, or both.

In embodiments in which a polymer possessing reactive groups is applied to a component of the wound closure device and utilized to adhere the device to tissue, the polymer possessing a reactive group may be applied to a device utilizing any method within the purview of those skilled in the art. For example, the implant may be combined with a composition having at least one free reactive group capable of chemically bonding with living tissue. Chemical bonding with living tissue will immobilize the device to the tissue and reduce the need to utilize other mechanical or physical attachment devices, such as staples, tacks, sutures, and the like to attach the device. The amount of time for the reactive composition to bind to tissue may vary from about 5 seconds to about 24 hours, in embodiments from about 60 minutes to about 12 hours.

Alternatively, adhesion of the elongate body or plug member to the tissue may also be provided by mechanical means, including for example, micro-texture (gecko feet) or barbs. In an embodiment, a knit fabric or mesh may include spiked naps which protrude perpendicularly with respect to the mesh to penetrate and fasten to the device. Examples of such fabrics and textiles include those disclosed in U.S. Pat. No. 7,331,199, the entire disclosure of which is incorporated by reference herein.

Suitable materials of the present disclosure can be processed by methods within the purview of those skilled in the art including, but not limited to: extrusion; injection molding; compression molding; blow molding; film blowing; thermoforming; calendaring; spinning; and film casting.

Additionally, any part of the device may include biologically acceptable additives such as plasticizers, antioxidants, dyes, image-enhancing agents, dilutants, bioactive agents such as pharmaceutical and medicinal agents, and combinations thereof which can be coated on the wound closure device or impregnated within the resin or polymer.

Medicinal agents which may be incorporated into the wound closure device may include, but are not limited to, antimicrobial agents, anti-virals, anti-fungals, and the like. Antimicrobial agents as used herein is defined by an agent which by itself or through assisting the body (immune system) helps the body destroy or resist microorganisms which may be pathogenic (disease causing). The term "antimicrobial agent" includes, e.g., antibiotics, quorum sensing blockers, surfactants, metal ions, antimicrobial proteins and peptides, antimicrobial polysaccharides, antiseptics, disinfectants, anti-virals, anti-fungals, quorum sensing blockers, and combinations thereof.

Examples of suitable antiseptics and disinfectants which may be combined with the present disclosure include hexachlorophene, cationic biguanides like chlorohexadine and cyclohexidine, iodine and iodophores like povidone-iodine, halo-substituted phenolic compounds like PCMX (e.g., p-chloro-m-xylenon) and triclosan (e.g., 2,4,4'-trichloro-2'hydroxy-diphenylether), furan medical preparations like nitrofurantoin and nitrofurazone, methanamine, aldehydes like gluteraldehyde and formaldehyde, alcohols, combinations thereof, and the like. In some embodiments, at least one of the antimicrobial agents may be an antiseptic, such as triclosan.

Classes of antibiotics that can be combined with the present disclosure include tetracyclines like minocycline, rifamycins like rifampin, macrolides like erythromycin, penicillins like nafcillin, cephalosporins like cefazolon, beta-lactam antibiotics like imipenen and aztreonam, aminoglycosides like gentamicin and TOBRAMYCIN®, chloramphenicol, sulfonamides like sulfamethoxazole, glycopeptides like vancomycin, quilones like ciproflaxin, fusidic acid, trimethoprim, metronidazole, clindamycin, mupirocin, polyenes like amphotericin B, azoles like fluconazole, and beta-lactam inhibitors like sublactam. Other antimicrobials which may be added include, for example antimicrobial peptides and/or proteins, antimicrobial polysaccharides, quorum sensing blockers (e.g., brominated furanones), antivirals, metal ions such as ionic silver and ionic silver glass, surfactants, chemotherapeutic drug, telomerase inhibitors, other cyclic monomers including 5-cyclic monomers, mitoxantrone, and the like.

In some embodiments, suitable bioactive agents which may be used include colorants, dyes, preservatives, protein and peptide preparations, protein therapeutics, polysaccharides such as hyaluronic acid, lectins, lipids, probiotics, angiogenic agents, anti-thrombotics, anti-clotting agents, clotting agents, analgesics, anesthetics, wound repair agents, chemotherapeutics, biologics, anti-inflammatory agents, anti-proliferatives, diagnostic agents, antipyretic, antiphlogistic and analgesic agents, vasodilators, antihypertensive and antiarrhythmic agents, hypotensive agents, antitussive agents, antineoplastics, local anesthetics, antispasmatics, hormone preparations, antiasthmatic and antiallergic agents, antihistaminics, anticoagulants, antispasmodics, cerebral circulation and metabolism improvers, antidepressant and antianxiety agents, vitamin D preparations, hypoglycemic agents, antiulcer agents, hypnotics, antibiotics, antifungal agents, sedative agents, bronchodilator agents, antiviral agents, dysuric agents, brominated or halogenated furanones, and the like. In embodiments, polymer drugs, e.g., polymeric forms of such compounds for example, polymeric antibiotics, polymeric antiseptics, polymeric chemotherapeutics, polymeric anti-proliferatives, polymeric antiseptics, polymeric non-steroidal anti-inflammatory drugs (NSAIDS), and the like may be utilized and combinations thereof.

In certain embodiments, wound closure devices of the present disclosure may contain suitable medicinal agents such as viruses and cells, peptides, polypeptides and proteins, analogs, muteins, and active fragments thereof, such as immunoglobulins, antibodies (monoclonal and polyclonal), cytokines (e.g. lymphokines, monokines, chemokines), blood clotting factors, hemopoietic factors, interleukins (IL-2, IL-3, IL-4, IL-6), interferons ($\beta$-IFN, $\alpha$-IFN and $\gamma$-IFN), erythropoietin, nucleases, tumor necrosis factor, colony stimulating factors (e.g., GCSF, GM-CSF, MCSF), insulin, anti-tumor agents and tumor suppressors, blood proteins, gonadotropins (e.g., FSH, LH, CG, etc.) hormones and hormone analogs (e.g., growth hormone), vaccines (e.g., tumoral, bacterial and viral antigens), somatostatin, antigens, blood coagulation factors, growth factors, protein inhibitors, protein antagonists, and protein agonists, nucleic acids, such as antisense molecules, DNA, RNA, oligonucleotides, polynucleotides and ribozymes and combinations thereof.

In some embodiments, additives such as image-enhancing agents (e.g., contrast agents) and more specifically, radiopaque markers, may be incorporated into the medical device. These image-enhancing agents enable visualization of the wound closure device (against surrounding tissue), when imaged or scanned through different filters such as MRI, X-ray, fluoroscopy, CT, various light sources, and the like. In order to be opaque (and visualized in certain filters), the wound closure device may be made from a material possessing radiographic density higher than the surrounding host tissue and have sufficient thickness to affect the transmission of x-rays to produce contrast in the image. Useful image-enhancing agents include but are not limited to radiopaque markers such as tantalum, barium sulfate, bismuth trioxide, bromine, iodide, titanium oxide, zirconium, barium, titanium, bismuth, iodine, nickel, iron, silver, and combinations thereof. In some embodiments, compounds such as tantalum, platinum, barium and bismuth may be incorporated into the wound closure device. Often image-enhancing agents are not bioabsorbable or degradable but are excreted from the body or stored in the body.

Image-enhancing agents may be compounded into the materials (e.g., resin) as filler prior to processing including extrusion or molding. These agents may be added in various concentrations to maximize polymer processing while maximizing the material characteristics of the wound closure device. The biocompatible agents can be added in quantities sufficient to enhance radiopacity while maintaining the polymer's properties. In certain embodiments, image-enhancing agents may be incorporated into a biodegradable material, enabling surgeons to know when the biodegradable material has degraded.

Methods for combining the above mentioned bioactive agents with materials of the present disclosure are within the purview of those skilled in the art and include, but are not limited to mixing, blending, compounding, spraying, wicking, solvent evaporating, dipping, brushing, vapor deposition, coextrusion, capillary wicking, film casting, molding and the like. Additionally, solvents may be used to incorporate various agents (e.g., bioactive agents) into the composite device. Suitable solvents include alcohols, e.g., methanol, ethanol, propanol, chlorinated hydrocarbons (such as methylene chloride, chloroform, 1,2-dichloro-ethane), and aliphatic hydrocarbons such as hexane, heptene, ethyl acetate.

The above description contains many specifics; these specifics should not be construed as limitations on the scope of the disclosure herein but merely as exemplifications of particularly useful embodiments thereof. Those skilled in the art will envision many other possibilities within the scope and spirit of the disclosure as defined by the claims appended hereto.

What is claimed is:

1. A wound closure device comprising:
   an elongate body including a proximal end and a distal end, and having a plurality of barbs extending from a surface thereof;
   a plug member including a proximal portion having a tissue facing surface and a distal portion, the plug member molded around the distal end of the elongate body such that the plug member is disposed at a distal-most end of the wound closure device and the elongate body extends proximally through the tissue facing surface of the plug member, the tissue facing surface is planar and the proximal portion has a larger dimension than the distal portion, the plug member including a mesh layered on the tissue facing surface, the plug member having a first, compressed shape for delivery and a second, expanded shape for placement; and
   an inner member slidably mounted on the elongate body, the inner member including a proximal-most end defining a largest dimension of the inner member and a distal-most end defining a smallest dimension of the inner member, the distal-most end of the inner member facing the tissue facing surface of the proximal portion of the plug member.

2. The wound closure device according to claim 1, wherein the plug member is formed from a biodegradable material and the mesh is formed from a non-biodegradable material.

3. The wound closure device according to claim 1, wherein the elongate body, the plug member, or both, comprise at least one free reactive group for binding to tissue.

4. The wound closure device according to claim 3, wherein the at least one free reactive group comprises an electrophilic functional group.

5. The wound closure device according to claim 3, wherein the at least one free reactive group is selected from the group consisting of isocyanate, N-hydroxy succinimide, cyanoacrylate, aldehyde, genipin, diisocyanate, carbodiimide, dimethyl adipimidate, sulfosuccinimides, carbonyldiimidazole, sulfonyl chloride, aryl halides, sulfosuccinimidyl esters, N-hydroxysuccinimidyl esters, succinimidyl esters, epoxides, aldehydes, maleimides, imidoesters, and combinations thereof.

6. The wound closure device according to claim 1, wherein the mesh includes at least one free reactive group for binding to tissue.

7. The wound closure device according to claim 1, wherein the inner member is formed from a biodegradable material.

8. The wound closure device according to claim 1, wherein the elongate body is a suture.

9. The wound closure device according to claim 1, wherein the plug member has a conical or hemispherical shape.

10. The wound closure device according to claim 1, wherein the inner member is funnel shaped and tapers from the proximal-most end to the distal-most end of the inner member.

11. The wound closure device according to claim 10, wherein the inner member defines an opening therethrough and the elongate body extends through the opening, the opening having a first diameter at the proximal-most end of the inner member and a second diameter at the distal-most end of the inner member, the first diameter being larger than the second diameter.

12. The wound closure device according to claim 10, wherein the inner member includes an outer surface tapering from the proximal-most end to the distal-most end, the outer surface being a tissue facing surface opposed from the tissue facing surface of the plug member to sandwich tissue therebetween.

13. The wound closure device according to claim 1, wherein the tissue facing surface of the plug member extends around the elongate body in touching relation therewith.

* * * * *